US012685492B2

(12) United States Patent (10) Patent No.: US 12,685,492 B2

Weiss et al. (45) Date of Patent: Jul. 21, 2026

(54) SYNCHRONISATION SYSTEM WITH TRIGGER DELAY

(71) Applicant: KONINKLIJKE PHILIPS N.V., Eindhoven (NL)

(72) Inventors: Steffen Weiss, Hamburg (DE); Wenjin Wang, Eindhoven (NL); Albertus Cornelis Den Brinker, Eindhoven (NL); Albert Garcia Tormo, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 194 days.

(21) Appl. No.: 18/578,757

(22) PCT Filed: Jul. 11, 2022

(86) PCT No.: PCT/EP2022/069216
§ 371 (c)(1),
(2) Date: Jan. 12, 2024

(87) PCT Pub. No.: WO2023/001606
PCT Pub. Date: Jan. 26, 2023

(65) Prior Publication Data
US 2024/0324971 A1 Oct. 3, 2024

(30) Foreign Application Priority Data
Jul. 20, 2021 (EP) ..................................... 21186781

(51) Int. Cl.
*G01V 3/00* (2006.01)
*A61B 5/00* (2006.01)
*A61B 5/055* (2006.01)

(52) U.S. Cl.
CPC ............ *A61B 5/7292* (2013.01); *A61B 5/055* (2013.01); *A61B 5/7264* (2013.01)

(58) Field of Classification Search
CPC ............ G01R 33/3607; G01R 33/5608; G06T 11/005; G06T 11/006; G06T 2211/424
(Continued)

(56) References Cited

U.S. PATENT DOCUMENTS

2008/0309881 A1* 12/2008 Huang ................... A61B 3/024
382/131
2010/0249574 A1 9/2010 Miyazaki
(Continued)

FOREIGN PATENT DOCUMENTS

CN 101111781 B * 2/2011 ........... G01T 1/2985
CN 104220129 A * 12/2014 ......... A61N 1/36053
(Continued)

OTHER PUBLICATIONS

International Search Report and Written Opinion from PCT/EP2022/069216 mailed Oct. 14, 2022.
(Continued)

*Primary Examiner* — Walter L Lindsay, Jr.
*Assistant Examiner* — Frederick Wenderoth

(57) ABSTRACT

A synchronisation system comprises aa sensor arrangement to detect a trigger base event. An analysis module and an arithmetic unit are configured to access prior information on a time delay between the sensor arrangement's detection of the trigger base and a starting point of an acquisition time interval for acquiring imaging data. The starting point is computed of the acquisition time interval from the detected trigger base event and the prior information of the time delay. The time delay between the sensor arrangement's detection of the trigger base event and the acquisition time interval may vary between individual subjects, but for each individual subject the time delay is well reproducible and hence on a per subject basis may be calibrated for.

9 Claims, 6 Drawing Sheets

(58) Field of Classification Search
USPC ......................................................... 324/309
See application file for complete search history.

(56) References Cited

U.S. PATENT DOCUMENTS

| | | | |
|---|---|---|---|
| 2010/0308823 A1 | 12/2010 | Sugiura | |
| 2016/0331239 A1 | 11/2016 | Maclaren et al. | |
| 2020/0046300 A1 | 2/2020 | Senegas et al. | |

FOREIGN PATENT DOCUMENTS

| | | | | | |
|---|---|---|---|---|---|
| CN | 102483730 B | * | 5/2016 | ......... | H04L 63/0236 |
| CN | 109005113 A | * | 12/2018 | ............. | H04L 45/12 |
| CN | 110269618 A | | 9/2019 | | |
| EP | 3804618 A1 | | 4/2021 | | |
| JP | 2018504802 A | * | 2/2018 | ........... | G11B 27/031 |
| WO | WO-2016110804 A1 | * | 7/2016 | ........... | A61B 5/4815 |

OTHER PUBLICATIONS

Yao Jingting et al: "An Adaptive Seismocardiography (SCG)-ECG Multimodal Framework for Cardiac Gating Using Artificial Neural Networks", IEEE Journal of Translational Engineering in Health and Medicine, vol. 6, Oct. 26, 2018 (Oct. 26, 2018), pp. 1-11.

Martinek Radek et al: "A Low-Cost System for Seismocardiography-Based Cardiac Triggering: A Practical Solution for Cardiovascular Magnetic Resonance Imaging at 3 Tesla", IEEE Access, vol. 7, Sep. 5, 2019 (Sep. 5, 2019), pp. 118608-118629.

Nedoma et al "A Novel FBG-Based Triggering System for Cardiac MR Imaging at 3 Tesla: A Pilot Clinical Study" IEEE Acces, vol. 8, Sep. 30, 2020 p. 181205-181223.

Spicher et al "Initial Evaluation of Prospective Cardiac Triggering Using Photo Plethysmography Signals Recorded with a Video Camera Compared to Pulse Oximetry and Electrocardiogram at 7T MRI" Biomedical Engineering 2016 15(1) 126.

* cited by examiner

SYNCHRONISATION SYSTEM WITH TRIGGER DELAY

CROSS REFERENCE TO RELATED APPLICATIONS

This application is a U.S. national phase application of International Application No. PCT/EP2022/069216 filed on Jul. 11, 2022, which claims the benefit of EP Application Serial No. 21186781.7 filed on Jul. 20, 2021 and is incorporated herein by reference.

FIELD OF THE INVENTION

The invention pertains to a synchronisation system, notably for triggering acquisition of imaging data, that involves a trigger delay.

BACKGROUND OF THE INVENTION

Such a synchronisation is known from the paper by N. Spicher, M. Kukuk, S. Maderwald, and M. E. Ladd. "Initial evaluation of prospective cardiac triggering using photo plethysmography signals recorded with a video camera compared to pulse oximetry and electrocardiography 7T MRI", in Biomedical engineering online 2016; 15(1):126.

The known synchronisation system is in fact an experimental set up for synchronisation between MR imaging data (k-space data) acquisition and subject cardiac activity to reduce imaging artefacts due to (cardiac) motion. Contact free triggering is done by estimating the phase of the cardiac cycle from a remote photo plethysmography (rPPG)-signal obtained from skin colour variations with a video camera. That is, the above paper reports on MR image acquisition based on video triggers per se.

SUMMARY OF THE INVENTION

An object of the present invention is to provide a synchronisation that more accurately determines trigger base events that form the basis of synchronisation of imaging data acquisition with during subject motion.

This object is achieved by the sensor arrangement of the invention to detect a trigger base event comprising an analysis module and an arithmetic unit configured to
    access prior information on a time delay between the sensor arrangement's detection of the trigger base and a starting point of an acquisition time interval for acquiring imaging data and
    compute the starting point of the acquisition time interval from the detected trigger base event and the prior information of the time delay, wherein
    the analysis module and the arithmetic unit are configured to access the prior information in the image information of a subject to be examined and on the basis of the accessed image information to derive the time delay between the sensor arrangement's detection of the trigger base and a starting point of an acquisition time interval for acquiring imaging data.

An insight of the invention is that synchronisation systems that are based on the sensor arrangement that performs a relatively indirect measurement of the trigger base event incur a time delay between the actual occurrence of the trigger base event and the instant at which the sensor arrangement detects the trigger base event. A further insight of the present invention is that this time delay may be compensated for. The synchronisation system of this aspect of the invention comprises a sensor arrangement to detect a trigger base event that represents an upcoming acquisition time interval during which imaging data, such as MR k-space data or CT attenuation profiles, may be acquired by a tomographic (MRI, CT, NM (PET, SPECT) diagnostic imaging system at a low level or even absence of perturbations, e.g. due to motion of the subject to be imaged (patient to be examined). The sensor arrangement may be a camera system to record changes of the skin colour that reflect the heartbeat. The sensor arrangement may also be a simple conventional (IR) fingertip sensor. According to this aspect prior information is accessed on the time delay between the sensor arrangement's detection of the trigger base event and the occurrence of the acquisition time interval. The prior information includes image information that contains information or represents anatomical distances and sizes. Notably, these distances and sizes determine the path that blood needs to travel from the patient's heart to the location from which the skin colour change is recorded. That is, from the prior information, by image analysis (e.g. automatic pattern recognition or indication of anatomical landmarks by a human user) anatomical sizes and distances can be computed. Then, with the use of a pre-determined value or an estimate of the patient's blood flow-velocity the time delay between the sensor arrangements' detection of the trigger base event and the actual occurrence of the trigger base event can be computed. Alternatively, a trained neural network may be provided in the analysis module to return the time delay from the input image information. This forms a machine learning analysis module. This computation of the time delay from the image information may be done by way of a suitably trained machine-learning model or trained neural network. An explicit computation of anatomical distances from the image information is an implementation using relatively simple feature recognition and geometric calculations.

For example the trigger base event may be an R-peak in an electrocardiogram (ECG) of the patient's heart and the acquisition time interval may be the quiescent heart phase following the R-peak and in which the is no or little heart motion and the acquired k-space data or attenuation profiles are hardly or not at all affected by motion. It is an insight of the present aspect of the invention that the time delay between the sensor arrangement's detection of the trigger base event and the acquisition time interval may vary between individual subjects, but for each individual subject the time delay is well reproducible and hence on a per subject basis may be calibrated for. The calibrated time delay allows to synchronise acquisition of imaging data with the motion of the subject such that image data can be acquired. Hence, in this aspect of the invention, acquisition of image data may be done on the basis of a trigger base event closely preceding the acquisition time interval. In a practical example the trigger base event may be an R-peak of an electrocardiogram and the acquisition interval may be in the quiescent phase closely subsequent to the detected R-peak. That is, the quiescent interval immediately after the detected R-peak may be used for the acquisition of the imaging data. From the calibrated time delay and the mean time interval between trigger base events, the image acquisition may be adapted to time available between the detection of the current trigger base event and the expected next trigger base event From the US-patent application US2010/0308823 it is known per se that the photo plethysmography (PPG)-signal appears with a time delay from the ventricular contraction. This delay may be estimated from blood-velocity changes from a separate measurement of pixel-wise blood velocity without using an ECG-signal.

In a further example of the synchronisation system of the invention, the computation of the starting point of the acquisition time interval also accounts for latency of the sensor arrangement. This is particularly effective where the sensor arrangement is implemented as a camera based sensor arrangement. This latency represents the technical delay caused by the technology of the sensor arrangement. For a camera, indeed, there may be delay of one to two frames until the sensor arrangement's software can determine that the blood rushes into the skin, e.g. on the patient's face. However, an insight of the present invention is that still, most of the sensor arrangement delay is caused by the pulse transit time from the heart to the face. Further details of corrections of the latency of the sensor arrangement are described in the European patent application EP20185605.1.

In another implementation of the synchronisation system the prior information on the time delay between the actual trigger base event and the timing of the acquisition interval is obtained from a separate (to the imaging data acquisition) calibration. In this calibration the trigger base event and the timing of the acquisition interval are directly measured. That is, in an examining separate from a synchronised acquisition of imaging data there are done (a) direct measurement of the actual instant of the trigger base event and of the acquisition time interval and (b) a simultaneously detecting the trigger base event by the sensor arrangement.

In this calibration, it may not be necessary to compare the direct measurement with the detection of the trigger base event by the actual individual sensor arrangement that is employed to synchronise acquisition of imaging data by the imaging system. Usually it is sufficient that the calibration involves the combination of a direct measurement and determination by a sensor arrangement that is sufficiently similar (same class of same type) to the individual sensor arrangement to be employed in in image acquisition at a later point in the patient's care cycle.

For example in cardiac MR imaging, as the trigger base events the R-peaks of the electrocardiogram are used. The direct measurement of the R-peak may be based on electronic measurements of the electrical activity of the heart by way of a set of electrodes placed on the patient's thorax. The acquisition interval is timed in the quiescent (mid to end) diastolic phase between successive R-peaks in the electrocardiogram. The electrocardiogram may be directly electronically measured by picking-up electronic cardiac signals by electrodes attached to the patient's thorax. Together with the direct detection of the trigger base events, the trigger base events are also detected by the sensor arrangement, which may be camera-based. From the comparison of the detection of the trigger base events by the sensor arrangement (arrangement) on the one hand and the direct measurement on the other hand, the time delay between the actual occurrence of the trigger base event and its detection by the sensor arrangement (arrangement) can be calibrated for. An insight of the present invention is that this time delay may vary between individual patients, while the time delay is well reproducing for a single individual patient. In practice, a direct measurement of trigger base events in the form of R-peaks of the electrocardiogram is done early in the care cycle of a patient. This direct measurement when combined with a detection of the trigger base event by the sensor arrangement (arrangement) provides the calibrated time delay that can also be employed in a subsequent imaging procedure. To that end an ECG recording system may be equipped with an additional photo plethysmography (PPG) sensor arrangement, which may be a camera-based PPG sensor arrangement or a conventional finger-tip sensor arrangement. Such an combined ECG-recording system with a PPG-sensor arrangement may be installed at a local point of care, such as a general practitioner's office. The camera-based PPG sensor arrangement detects variations in skin colour of the patient to be examined that represents pulsating blood flow. Usually skin colour is detected from the patient's face, e.g. forehead or temple. Alternatively or additionally, an adhesive contact PPG-sensor arrangement may be placed on the patient's skin. Further, also a conventional finger-tip PPG may be employed that is clamped to the patient's fingertip. Such a combined ECG-recording and PPG sensor arrangement can evaluate the patient specific delay between the actual trigger base event, i.e. the actual R-peak and a PPG-trigger marker detected by the PPG-sensor arrangement. This evaluation provides a calibration of the patient specific delay of the PPG-sensor arrangement to the actual R-peak recorded almost instantaneously by the ECG recording system based on electrodes on the patient's chest. This calibrated delay value may be employed subsequently in a PPG-based triggered magnetic resonance imaging protocol. The calibrated delay may also be employed for accurate time stamping magnetic resonance images relative to the R-peak forming the trigger base event. The calibrated delay between the PPG-sensor arrangement's recording of the trigger base event (R-peak) and the actual occurrence of the trigger base event by the PPG-sensor arrangement may be stored in the patient's digital health record and be made available during the subsequent magnetic resonance imaging procedure.

Further, the calibrated delay found form the comparison of the direct (ECG) measurement and the (PPG) sensor-based measurement may be compared to the delay that is computed from the image information on the subject that notably represents anatomical distances and sizes. This comparison provides a quantitative measure of the accuracy of the delay time derived from the image information.

The delay between the sensor arrangement's detection of the trigger base event (R-peak) and the trigger base event itself is caused by pulse transit time (PTT) from the heart to the PPG site and delays cardiac triggering. However, also here the face-based camera-PPG has an advantage, because respective PTTs are significantly shorter than for finger-tip-PPG. The PTT is known to vary with various physiological parameters as heart rate and blood pressure. It is very common that a stress-ECG (e.g. during physical stress by cycling) is acquired at the general practitioner or cardiologist prior to referral to an magnetic resonance imaging examination. It is proposed to equip this stress-ECG device with a PPG-camera, or with a contact-PPG sensor arrangement at the temple which may be less susceptible to motion artefacts in the PPG signal. During the exam the heart rate varies significantly. It is proposed to map the above delay as a function of heart rate. This mapping may be used during the MR exam, where the current heart rate is known from the PPG-signal.

An aspect of the invention concerns a computer programme comprising instructions to access prior information on a time delay between the sensor arrangement's detection of the trigger base and a starting point of an acquisition time interval for acquiring imaging data and compute the starting point of the acquisition time interval from the detected trigger base event and the prior information of the time delay.

Another aspect of the invention concerns a computer programme comprising instructions to perform a direct measurement of the actual instant of the trigger base event and of the acquisition time interval, simultaneously detect the trigger base event by a sensor arrangement and determine a time delay between the actual instant of the trigger base event the detection of the trigger base event by the sensor arrangement.

Accordingly, according to these computer programme aspects of the invention, the invention may at least in part me implemented in software that is capable to bring about the technical effects of the invention when installed in the synchronisation system's processor or computer and to implement the calibration procedure in software.

According to the invention the delay between the sensor arrangement's detection of the trigger base event and the trigger base event itself (the trigger delay) is derived from image information on the subject. The image information represents anatomical information of the subject, such as body height, arm length, shoulder width, distances from the aortic valve to the patient's forehead or finger. This anatomical information is relevant for the determination of the trigger delay. The accessed image information may be (colour or greyscale, infrared) images acquired by a camera system. The camera system may be mounted outside the examination zone of the tomographic diagnostic imaging system and controlled to acquire the images during preparation of the subject to be examined in the tomographic diagnostic imaging system. The camera system may also be mounted in or next to the examination zone. Such an in-bore camera system may acquire the image information during the tomographic image procedure. The image information may also be accessed from a preparatory magnetic resonance image, such as a low-resolution survey image. This embodiment of the synchronisation achieves to accurately determine the trigger delay taking into account differences between individual patients. The accurate trigger delay may be employed to synchronise acquisition of imaging data by the tomographic diagnostic imaging system with recurring motion, such as the subject's cardiac motion. The accurate trigger delay may also be employed for correct timing of magnetisation preparation (e.g. inversion recovery, magnetisation transform techniques and black-blood angiography) and excitation in magnetic resonance imaging. The accurate delay may also be employed to optimise scan efficiency by optimally using the time between the sensor arrangement's detection of a trigger base event and the subsequent trigger base event for magnetization preparation and image data acquisition.

In another example of the synchronisation system of the invention, the trigger delay is estimated based on anatomical sizes and distances. It appears that these parameters predominantly determine variations among subjects of the trigger delay. For example, the trigger delay may be due to the transit time of blood from the patient's heart to the anatomical location (forehead, fingertip). In a further implementation, an estimation of the trigger delay may be performed by machine learning (e.g. a convolutional network). This may be achieved in two variants: a) direct estimation of the delay by the network with the image as input parameter or b) estimation of the anatomical features as arm length by the network based on the input image. and regression of the delay based on these anatomical features.

In a further implementation of the synchronisation system of the invention also at least two trigger base events e.g. based on PPG measurements at different locations are used to estimate the pulse transit velocity PTV. This approach is based on the insight that the PTV also depends on physiological parameters such as stiffness of the arteries and blood pressure. Based on the PTV and known anatomical distances as from heart to face, the pulse delay of the detection of the trigger base event e.g. by way PPG measurement at the patient's face is calculated.

A further aspect of the invention concerns a computer programme comprising instructions to control a sensor arrangement to detect trigger base events at different locations in a subject's body to be examined and to derive a pulse transit velocity from the time differences between the detected trigger base events and the derived anatomical distances between these different locations. According to this aspect of the invention, the derivation of the pulse transit velocity may be implemented in software. A further aspect of the invention concerns a computer programme comprising instructions to access image information on a subject to be examined and to derive on the basis of the accessed image information the time delay between the sensor arrangement's detection of the trigger base and a starting point of an acquisition time interval for acquiring imaging data. According to this aspect of the invention the derivation of the time delay from image information may be implemented in software. These and other aspects of the invention will be further elaborated with reference to the embodiments defined in the dependent Claims.

These and other aspects of the invention will be elucidated with reference to the embodiments described hereinafter and with reference to the accompanying drawing wherein

DETAILED DESCRIPTION OF THE EMBODIMENTS

Figure 1:
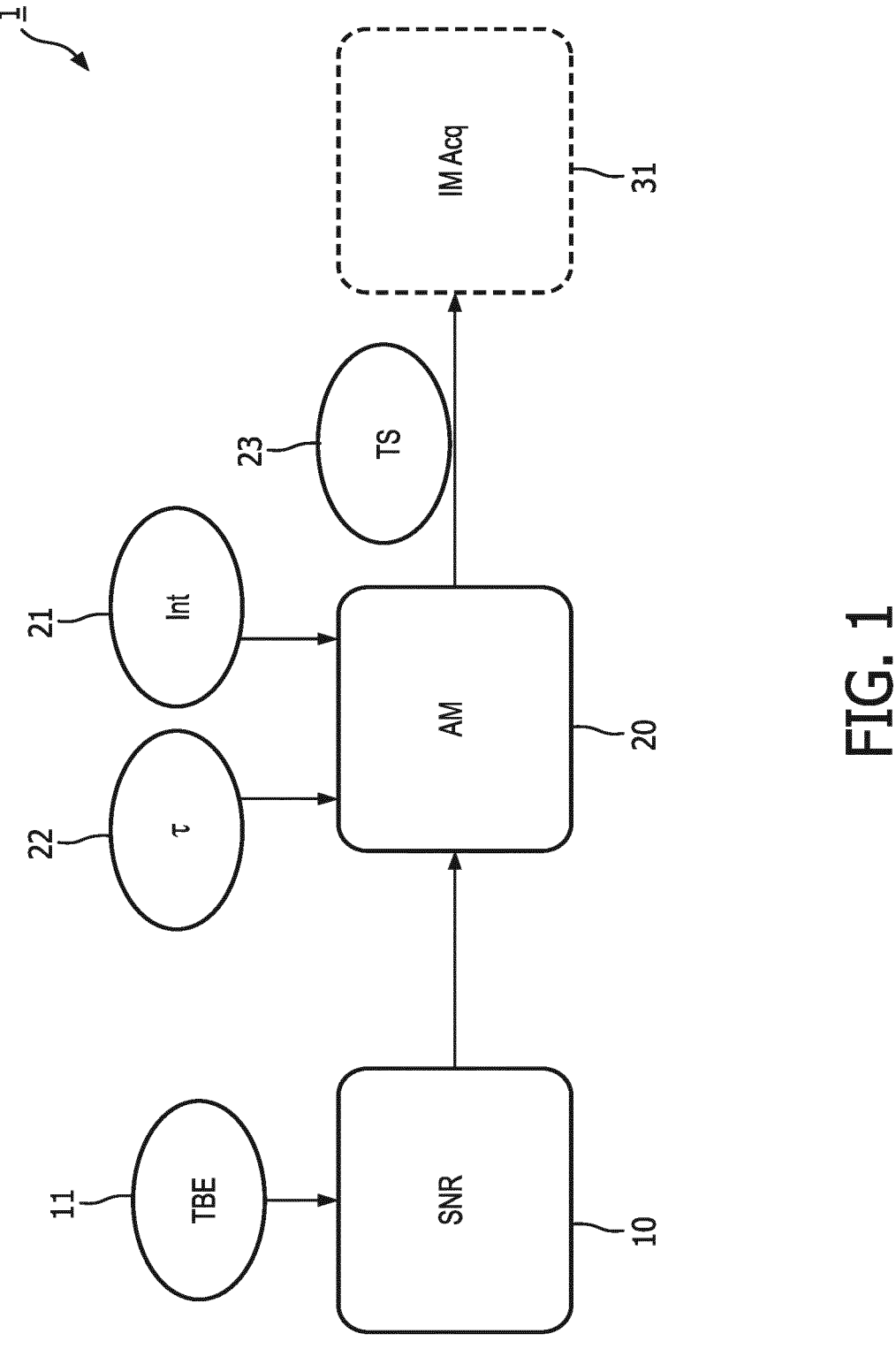
FIG. 1 shows a schematic representation of a synchronisation system of the invention.

FIG. 1 shows a schematic representation of the synchronisation system 1 of the invention. The synchronisation system functions to estimate a subsequent trigger base event from a detected current trigger base event (TBE) 11. The trigger base events are instances that prompt to trigger image acquisition e.g. by a tomographic imaging system 31. The tomographic imaging system may be a magnetic resonance examination system, a computed tomography system of a nuclear medicine tomographic imaging system. The acquired imaging information may be k-space profiles, attenuation profiles or detected gamma (γ) photons. A magnetic resonance image may be reconstructed form the k-space profiles, a computed tomography image may be reconstructed from (x-ray) attenuation profiles at various orientations. From the detected γ-photons a nuclear medicine tomographic image may be reconstructed. The imaging information in the form of k-space profiles, attenuation profiles or detected photons may be acquired in multiple sets of imaging data at successive intervals, notably during successive equal or comparable motion states of the subject to be imaged (patient to be examined). For example imaging data sets may be acquired an equal, comparable of corresponding cardiac or respiratory phases. The synchronisation system is provided with the sensor 10 to detect a current trigger base event 11. The synchronisation system 1 is provided with an analysis model 20 to which the detected trigger base event's instant is applied by the sensor 10. The analysis module has access to prior information on the latency of the sensor (τ) 22 and the time interval (Int) 21 between the actual trigger base event and the timing of the acquisition interval. This prior information may be obtained from a previous (to the imaging data acquisition) calibration. The analysis module includes an arithmetic unit or a machine-learning unit to compute or return the trigger signal (TS) from the detected instant of the trigger base event and the prior information. The trigger signal is applied to a control unit of the image acquisition system 31. The synchronisation system may be integrated in the image acquisition system of may be a stand-alone synchronisation system coupled to the image acquisition system for the triggered image acquisition in point.

Figure 2:
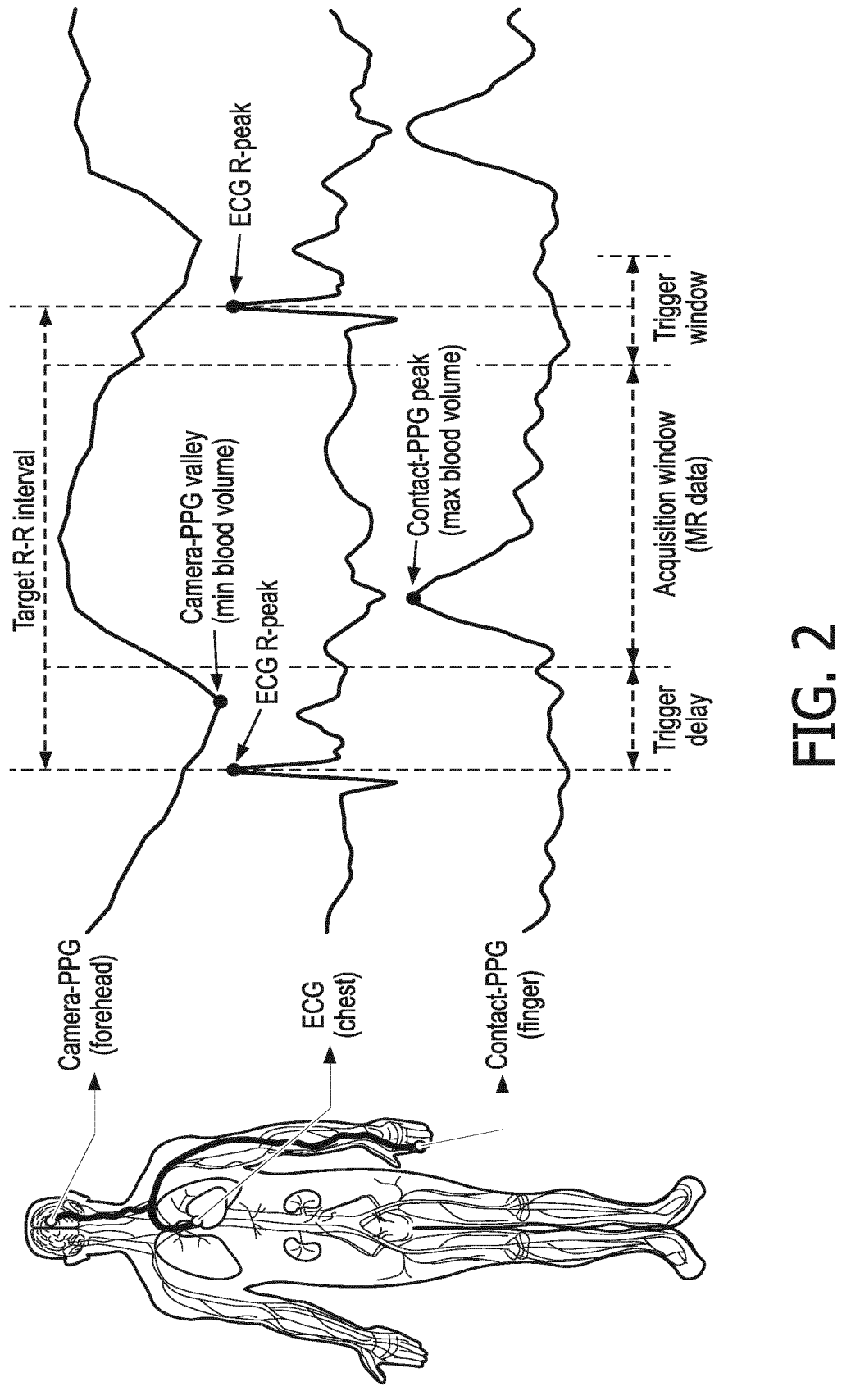
FIG. 2 illustrates an example of a camera-PPG signal from the face of a contact sensor at the finger and the underlying physiology that causes the time delay.

FIG. 2 illustrates an example of a camera-PPG signal from the face, an ECG signal, and a contact-PPG signal from the finger, all measured simultaneously during about one cardiac cycle. "Camera-PPG valley" and "Contact-PPG peak" denote PPG markers suitable for cardiac triggering. They are delayed with respect to the R-peak which is conventionally used for triggering. FIG. 2 illustrates that the trigger base event as detected by the ECG directly from electrodes placed on the patient's chest is detected with a negligible trigger delay. The trigger base event detected by the camera from the subject's forehead or by a contact sensor at the fingertip are delayed by respective trigger delays relative to the directly detected ECG R-peak.

Figure 3:
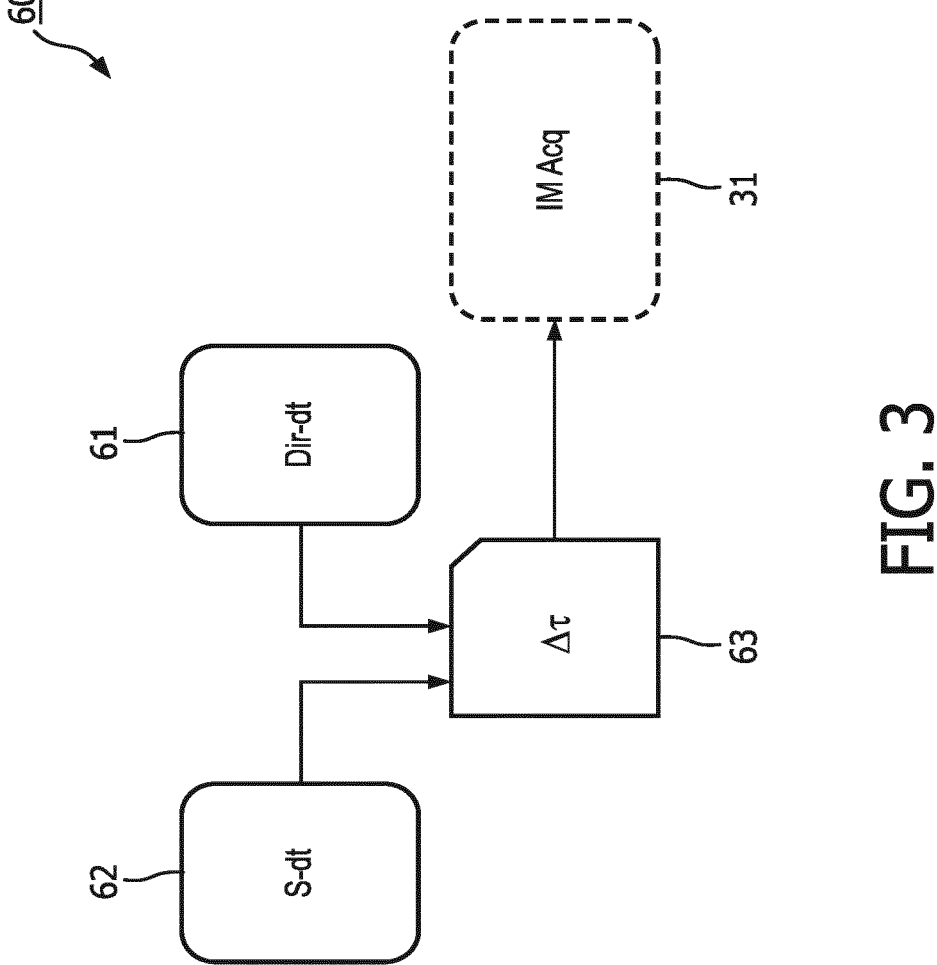
FIG. 3 shows a schematic representation of the calibration of the time delay for the synchronisation system of the invention.

FIG. 3 shows a schematic representation of the calibration of the time delay for the synchronisation system of the invention. This calibration relies on the insight illustrated with reference to FIG. 2. The calibration procedure 60 involves to perform a direct detection 61, i.e. having a priori a negligible trigger delay, to the trigger base event. That is the direct detection 61 is done by a measurement set up that has negligible technical sensor delay and also negligible pules transit time associated with the subject's physiology. Additionally, the trigger base event (same or corresponding) is detected 62 by the sensor arrangement (same or correspondingly equivalent) and the trigger delay is determined from the comparison of the detection instant and the direct detection and the detection by the sensor arrangement. This trigger delay represents the time span between the sensor arrangement detection of the trigger base event and the actual occurrence of the trigger base event in a reproducible manner for the individual subject at issue. Thus the calibrated trigger delay may be employed as the prior information in subsequent synchronisation, e.g. of diagnostic image acquisition. Further refinements may be made to correct the trigger delay for difference in heart rate of the subject during calibration and during synchronisation of the diagnostic image acquisition.

Figure 4:
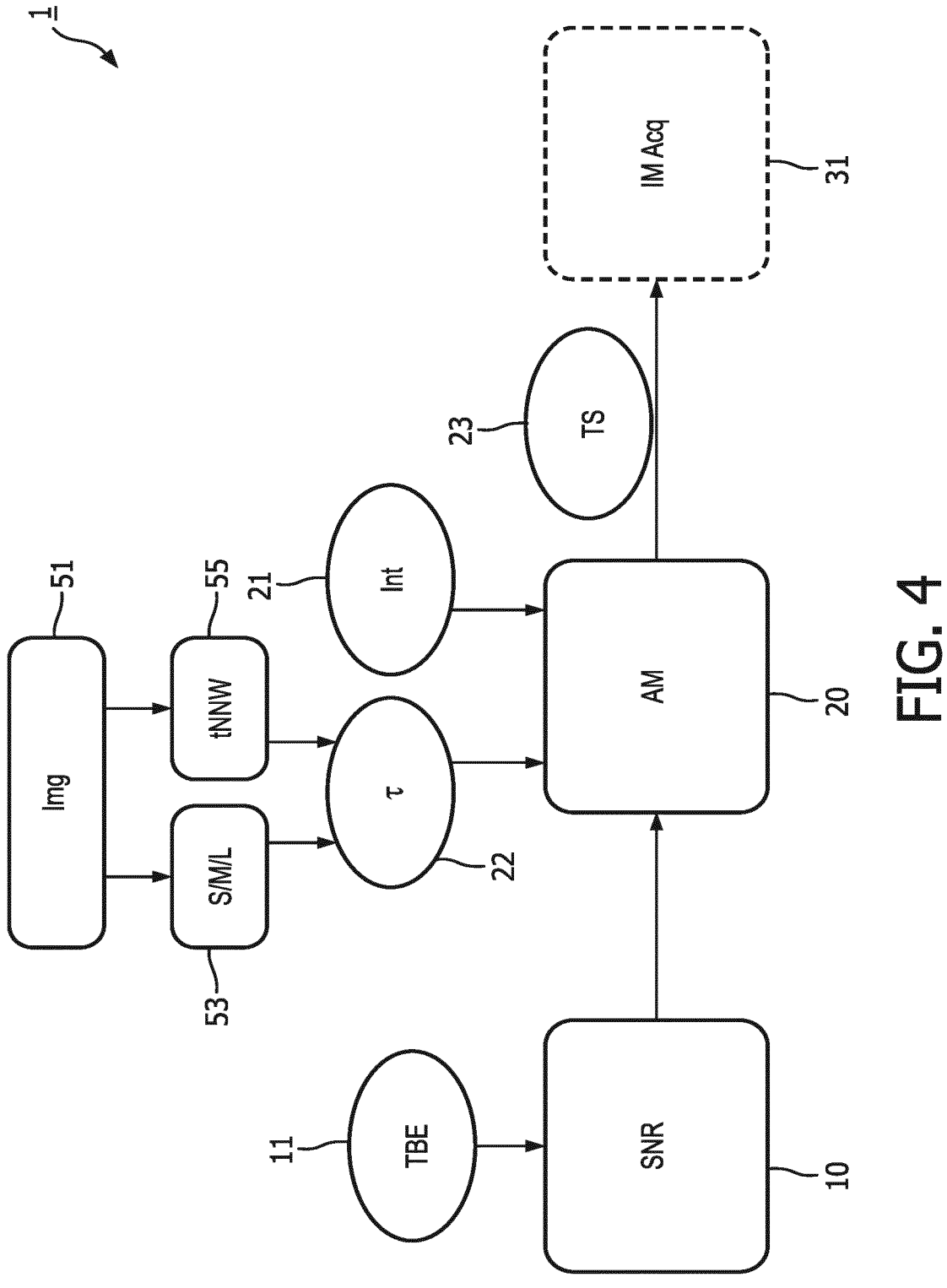
FIG. 4 shows a schematic representation of an implementation of the synchronisation system of the invention in which use is made of image information.
Figure 5:
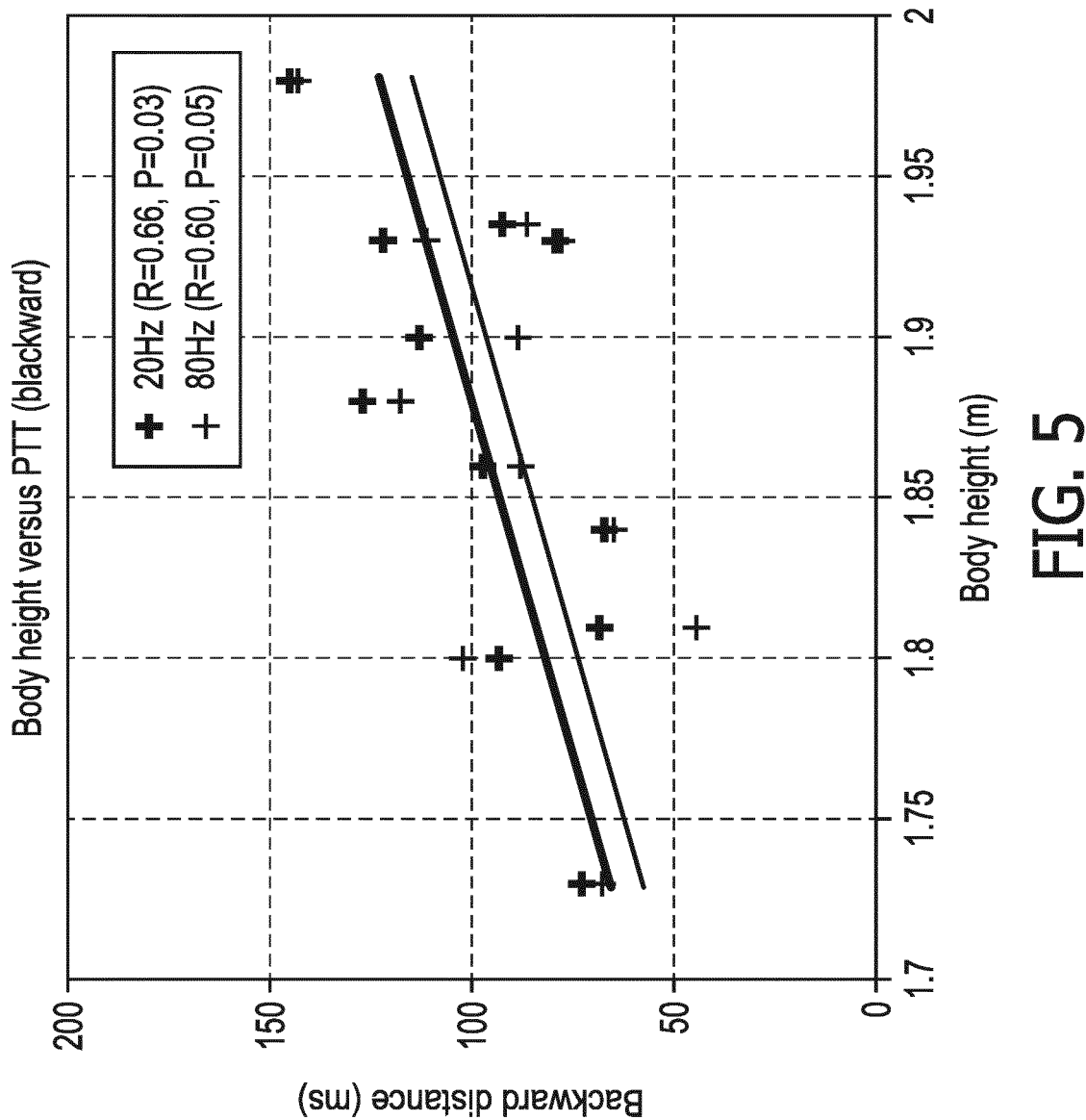
FIG. 5 shows an example of linear regression of the delay between the PPG trigger obtained from the face and the R-peak (here called "backward distance" or "PTT") versus body height as obtained in a volunteer study and FIG. 6 shows a schematic representation of an implementation of the synchronisation system of the invention in which individual trigger base events are detected from different positions on the body of the patient to be examined.

FIG. 4 shows a schematic representation of an implementation of the synchronisation system of the invention in which use is made of image information. Image information 51 may have been acquired by a camera or from a magnetic resonance or computed tomography (survey) image. From the image information 51 a geometry analyser 53 derives anatomical distances that are applied to the analysis module. Alternatively, a trained neural network 55 returns anatomical distances from the input image information 51. The trained neural network may be trained on the basis of training datasets of sets of images and separately measured anatomical distances of the anatomies represented by the images. On the basis of the anatomical distances, the analysis module 20 estimates the trigger delay. This may be done on the basis of a simple computation using a representative value of blood velocity or by way of a look-up-table stored in or accessed by the analysis module 20. The trigger delay may be estimated on the basis of a linear regression analysis of calibration measurements of body height versus actual trigger delay or pulse transit time. Empirically the pulse transit time appears to be approximately linear with body height. This is illustrated in FIG. 5 which shows an example of linear regression of the delay between the PPG trigger obtained from the face and the R-peak (here called "backward distance" or "PTT") versus body height as obtained in a volunteer study. The labels 80 Hz and 20 Hz refer to the camera frame rates employed in the camera-based detection of the R-peaks. In this experiment the camera is located above the patient table. This camera may be used to obtain the image from which body height, shoulder width, arm length, etc. are obtained. The fixed installation of the camera and geometrical calibration allows to derive absolute sizes directly from the image. This can be done by known state-of-the-art image processing, or by machine learning.

Figure 6:
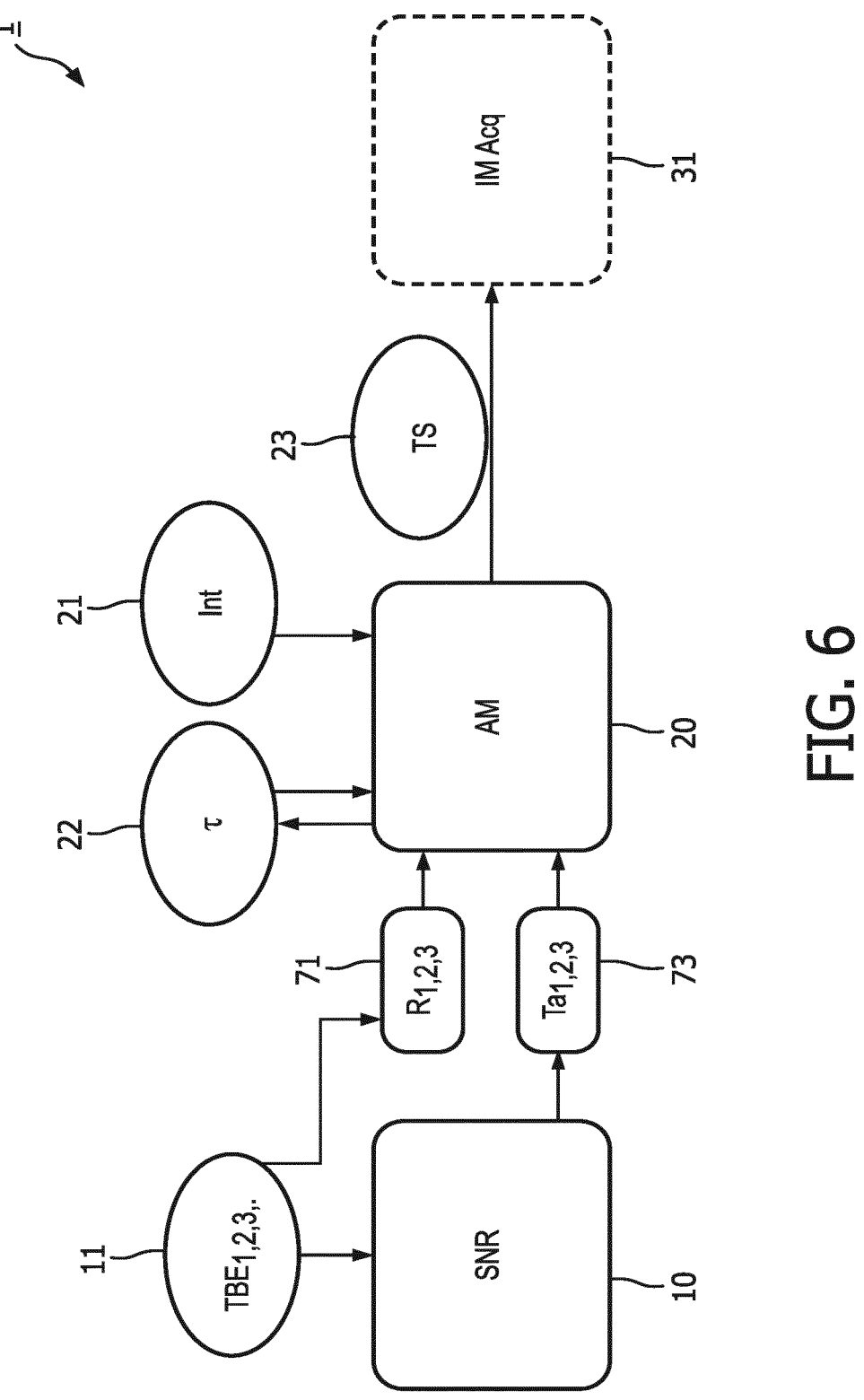

FIG. 6 shows a schematic representation of an implementation of the synchronisation system of the invention in which individual trigger base events are detected from different positions on the body of the patient to be examined. In this implementation the sensor includes multiple sensor elements that detect the individual trigger base event at different locations $R_{1,2,3}$ . . . 71 on the patient's body. The sensor elements detect the trigger base events from the respective locations at respective arrival times $Ta_{1,2,3}$ . . . 73. From the arrival times 73 and the detection locations 71, the analysis module may compute the pulse transit velocity PTV. Based on the PTV and known anatomical distances as from heart to face, the pulse delay of the PPG measurement at the patient's face is calculated.

The invention claimed is:

1. A synchronization system comprising
a sensor arrangement configured to detect a trigger base,
an analysis module configured to access prior information on a time delay between the sensor arrangement's detection of the trigger base and an arithmetic unit to compute a starting point of an acquisition time interval for acquiring imaging data and
compute the starting point of the acquisition time interval from the detected trigger base event and the prior information of the time delay wherein the analysis module and the arithmetic unit are configured to access the prior information in the form of image information on a subject to be examined and on the basis of the accessed image information derive the time delay between the sensor arrangement's detection of the trigger base and a starting point of an acquisition time interval for acquiring imaging data.

2. A computer program stored on a non-transitory computer readable medium, wherein the computer program is configured to control the synchronization system of claim 1 and comprising instructions to:

access the prior information on a time delay between the sensor arrangement's detection of the trigger base and the starting point of an acquisition time interval for acquiring imaging data and compute the starting point of the acquisition time interval from the detected trigger base event and the prior information of the time delay.

3. A computer program stored on a non-transitory computer readable medium, wherein the computer program is configured to control calibration of the time delay for the synchronization system of claim 1 and comprising instructions to:

perform the direct measurement of the actual instant of the trigger base event and of the acquisition time interval, simultaneously detect the trigger base event by a sensor arrangement and determine the time delay between the actual instant of the trigger base event and the detection of the trigger base event by the sensor arrangement.

4. The synchronization system of claim 1, wherein the analysis module and the arithmetic unit are configured to derive anatomical distances and sizes of the subject to be examined from the accessed image information and derive said time delay form the derived anatomical distances and sizes.

5. The synchronization system of claim 1, wherein the analysis module is provided with a machine-learning module to return said time delay from the accessed image information.

6. The synchronization system of claim 1, wherein the computation of the starting point of the acquisition time interval also accounts for the sensor arrangement's latency time.

7. The synchronization system of claim 1, wherein the prior information on the time delay has been previously calibrated for a subject to be examined by imaging in a calibration procedure to measure the acquisition time interval by a direct measurement of the trigger base event and the acquisition time interval.

8. A method of calibration of the time delay for a synchronization system of claim 1, wherein the acquisition time interval is measured in a calibration examining separate from a synchronised acquisition of imaging data and by:

(i) direct measurement of the actual instant of the trigger base event and of the acquisition time interval; and (ii) simultaneously detecting the trigger base event by the sensor arrangement.

9. The synchronization system of claim 1, wherein the sensor arrangement is controlled to detect trigger base events at different locations in a subject's body to be examined and the analysis module and the arithmetic unit are configured to derive a pulse transit velocity from the time differences between the detected trigger base events and the derived anatomical distances between these different locations.

\* \* \* \* \*